United States Patent [19]

Fort

[11] 4,121,458
[45] Oct. 24, 1978

[54] RELIABLE DYNAMOELECTRIC MACHINE CONDITION MONITOR

[75] Inventor: Emil M. Fort, Murrysville, Pa.

[73] Assignee: Westinghouse Electric Corp., Pittsburgh, Pa.

[21] Appl. No.: 771,713

[22] Filed: Feb. 24, 1977

[51] Int. Cl.² .......................... G01K 1/02; G01K 3/00
[52] U.S. Cl. ...................................... 73/339 R; 73/28
[58] Field of Search ........ 73/1 G, 28, 339 R, 339 TP, 73/432 PS; 310/86 C; 324/33

[56] References Cited

U.S. PATENT DOCUMENTS

| | | | |
|---|---|---|---|
| 3,114,877 | 12/1963 | Dunham | 73/28 X |
| 3,178,930 | 4/1965 | Moore et al. | 73/28 |
| 3,427,880 | 2/1969 | Grobel et al. | 73/339 R |
| 3,573,460 | 4/1971 | Skala | 73/339 R |
| 3,679,973 | 7/1972 | Smith, Jr. et al. | 73/28 X |

Primary Examiner—Charles A. Ruehl

Attorney, Agent, or Firm—G. H. Telfer

[57] ABSTRACT

Apparatus for sensing overheated electrical insulation through the detection of thermoparticulates in a dynamoelectric machine's cooling gas system is disclosed. The cooling gas as it circulates will entrain thermoparticulates produced in the system when there is overheating. This gaseous carrier is then withdrawn and conducted to an ionization chamber where it is ionized. Downstream from the ionization chamber there is placed a first ion collector for collecting ions with relatively small radii. A second ion collector which is biased for collecting ions with relatively large radii is also placed downstream from the ionization chamber. By comparison of ion current from the first ion collector with ion current from the second ion collector it is possible to detect the presence of thermoparticulates in the cooling gas relatively independent of gas pressure, flow rate through the monitor, and effectiveness of the radiation source.

6 Claims, 3 Drawing Figures

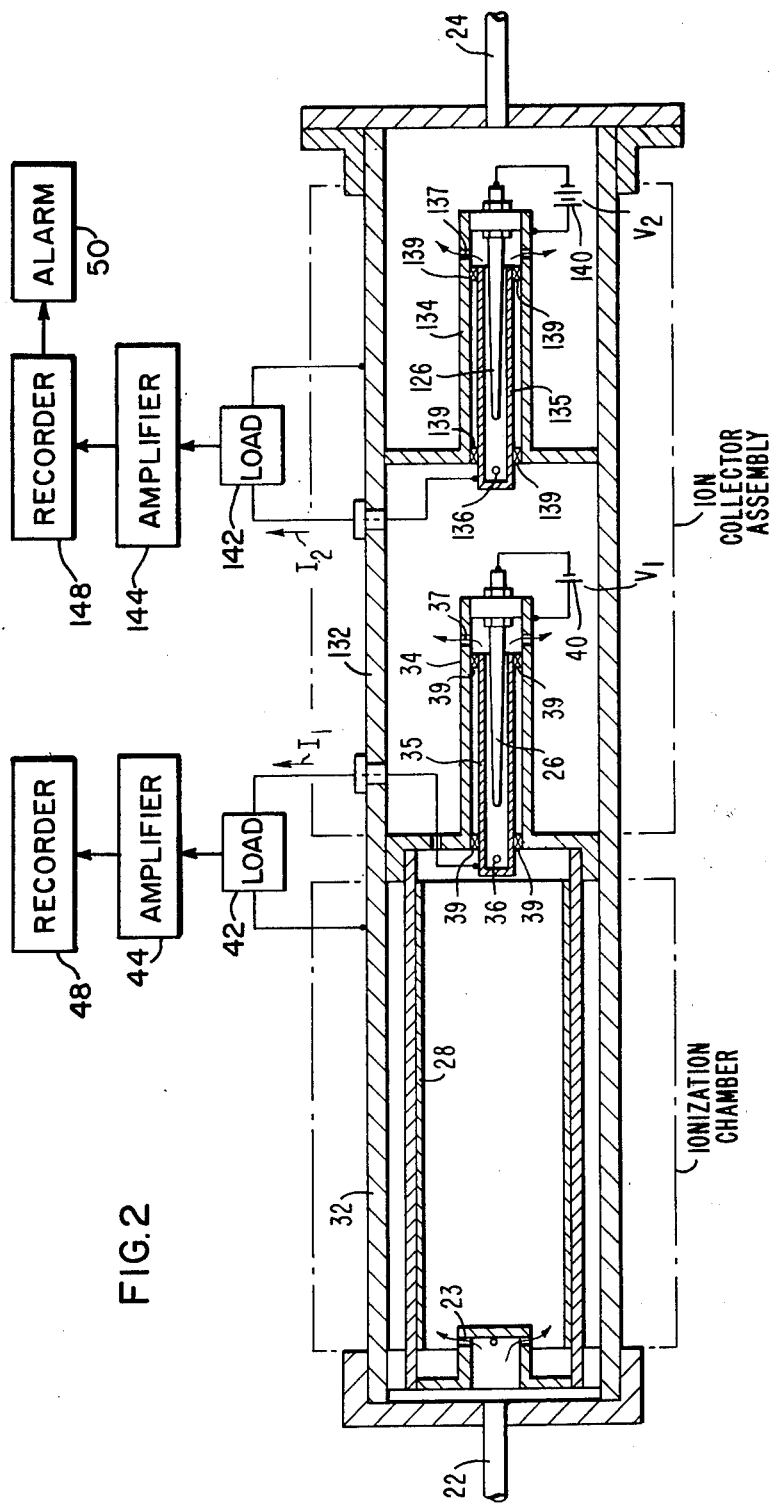

RELIABLE DYNAMOELECTRIC MACHINE CONDITION MONITOR

BACKGROUND OF THE INVENTION

1. Field of the Invention:

This invention relates to an apparatus for the detection of the overheating of electrical insulation and to gas cooled dynamoelectric machine systems incorporating such apparatus.

2. Description of the Prior Art:

During recent years, a device commonly known as a generator condition monitor (Ref: U.S. Pat. No. 3,427,880 issued Feb. 18, 1969 and U.S. Pat. No. 3,573,460 issued Apr. 6, 1971) has been used to detect overheating within a dynamoelectric machine, such as overheated electrical insulation, through the presence of thermoparticulates in the dynamoelectric machine's cooling gas. Thermoparticulates are formed in dynamoelectric machines as a product of thermal degradation of insulation. These particulates have radii of the order of between $1 \times 10^{-9}$ and $100 \times 10^{-9}$ meters. In the monitor, the molecules of a steadily flowing sample of the cooling gas are ionized to a state of equilibrium with a source of alpha-particles in an ionization chamber. The ions are then completely electrodeposited when the gas is passed between two charged electrodes in a collection chamber. The electrodeposition current is then amplified and applied to a recorder where it is continuously monitored. If there have been thermoparticulates entrained within a given sample, some of the ions will attach themselves to the thermoparticulates causing the number of free ions to decrease. The charged thermoparticulates have a much lower mobility as compared to the cooling gas ions; therefore, very few will be electrodeposited resulting in a decrease in the total electrodeposition current. This decrease is used as an indication of the presence of thermoparticulates caused by overheating.

A weakness of the generator condition monitor as described above and as it presently is used is that changes in the gas pressure, gas purity, or the flow through the monitor, as well as contamination of the radioactive source, can also cause a descrease of the electrodeposition current, thus falsely indicating a condition of overheating.

In copending Application Ser. No. 732,636, filed Oct. 15, 1976, by Dillman and assigned to the assignee of the present invention, now abandoned, there is disclosed an improved generator condition monitor. The Dillman invention generally comprises two streams which have been extracted from the cooling gas circulated through a generator and two thermoparticulate detectors operating in parallel with one detector monitoring one gas stream and the other detector monitoring the second gas stream after it has been filtered. Variation between the output signals of the detectors yields an overtemperature alarm which is independent of changes in the parameters of the cooling gas streams being monitored.

However, the Dillman invention requires servicing of the filters and manual intervention for verification of an alarm by inserting a filter in the unfiltered stream. If the alarm does not cease when the second filter is inserted, then the indication is that the alarm was false and one of the ionization chambers' radiation source is ineffective.

SUMMARY OF THE INVENTION

This application discloses apparatus for sensing overheated electrical insulation through the detection of thermoparticulates in a dynamoelectric machine's cooling gas and a dynamoelectric machine system incorporating such apparatus. The cooling gas as it circulates will entrain thermoparticulates produced in the system when there is overheating. This gaseous carrier is withdrawn and conducted to an ionization chamber where it is ionized. Downstream from the ionization chamber there is placed a first ion collector for collecting ions with relatively small radii. A second ion collector means which is biased for collecting ions with relatively large radii is also placed downstream from the ionization chamber. By comparison of the ion current from the first ion collector with the ion current from the second ion collector it is possible to detect the presence of thermal particulates in the cooling gas.

With the two collectors placed in series with each other, the first being biased for the small radii ions and the second collector being biased for large radii ions, only the second collector ion current need be monitored for detection of thermoparticulates.

Generally, if the collectors are placed either in series or in parallel, one collector is biased to collect ions with a radius of $2 \times 10^{-9}$ meters or less while the other collector is biased to collect ions with a radius of $85 \times 10^{-9}$ meters or less.

The apparatus therefore detects thermoparticulates within a dynamoelectric machine cooling gas in a manner that is relatively independent of gas pressure, flow rate through the monitor and effectiveness of the radiation source and requires a minimum of maintenance.

BRIEF DESCRIPTION OF THE DRAWINGS

The objects and advantages of this invention will become more apparent from reading the following detailed description in connection with the accompanying drawings in which corresponding reference characters indicate corresponding portions throughout the drawings and in which:

FIG. 2 is a simplified schematic view of the ionization chamber and two series connected ion collectors;

DESCRIPTION OF THE PREFERRED EMBODIMENTS

Figure 1:
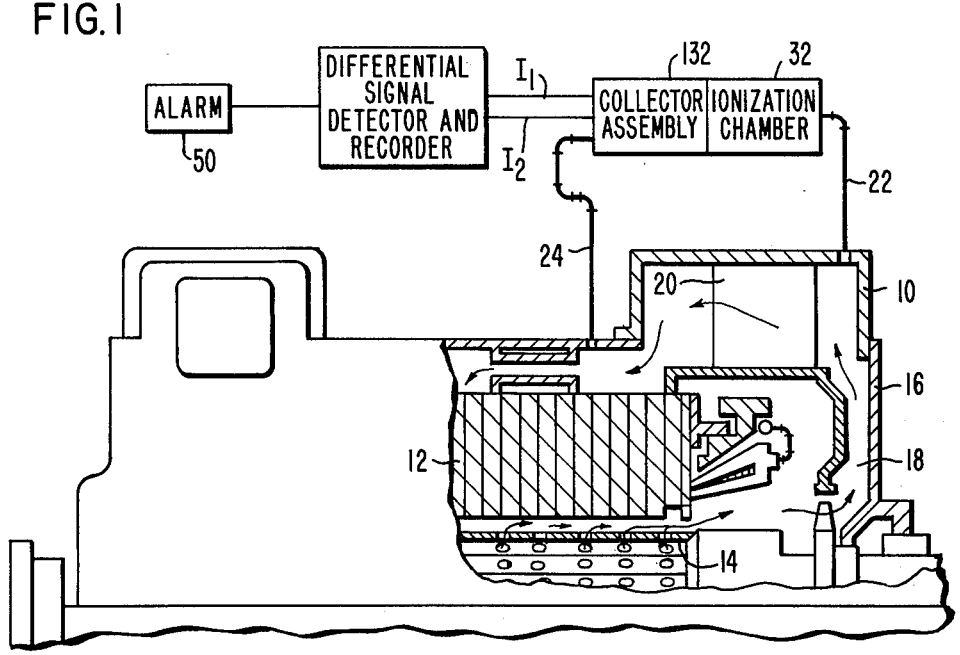
FIG. 1 is a simplified schematic view of a gas cooled generator, partly sectioned, illustrating how it is interconnected to an ionization chamber and the ion collector assembly.

Referring to the drawings in detail, FIG. 1 of the drawings shows a gas cooled generator 10 typical of a gas cooled electric machine with which the present invention can be used to detect overheating. Generator 10 includes a stator 12 and a rotor 14. The stator and the rotor are enclosed in a gas-tight casing 16 filled with a cooling gas, such as hydrogen, for example. A fan 18 draws cooling gas through generator parts such as rotor, stator, etc., with the gas being discharged by fan 18 into heat exchanger 20 where it is cooled and allowed to recirculate through the stator and rotor to the suction side of fan 18.

Figure 3:
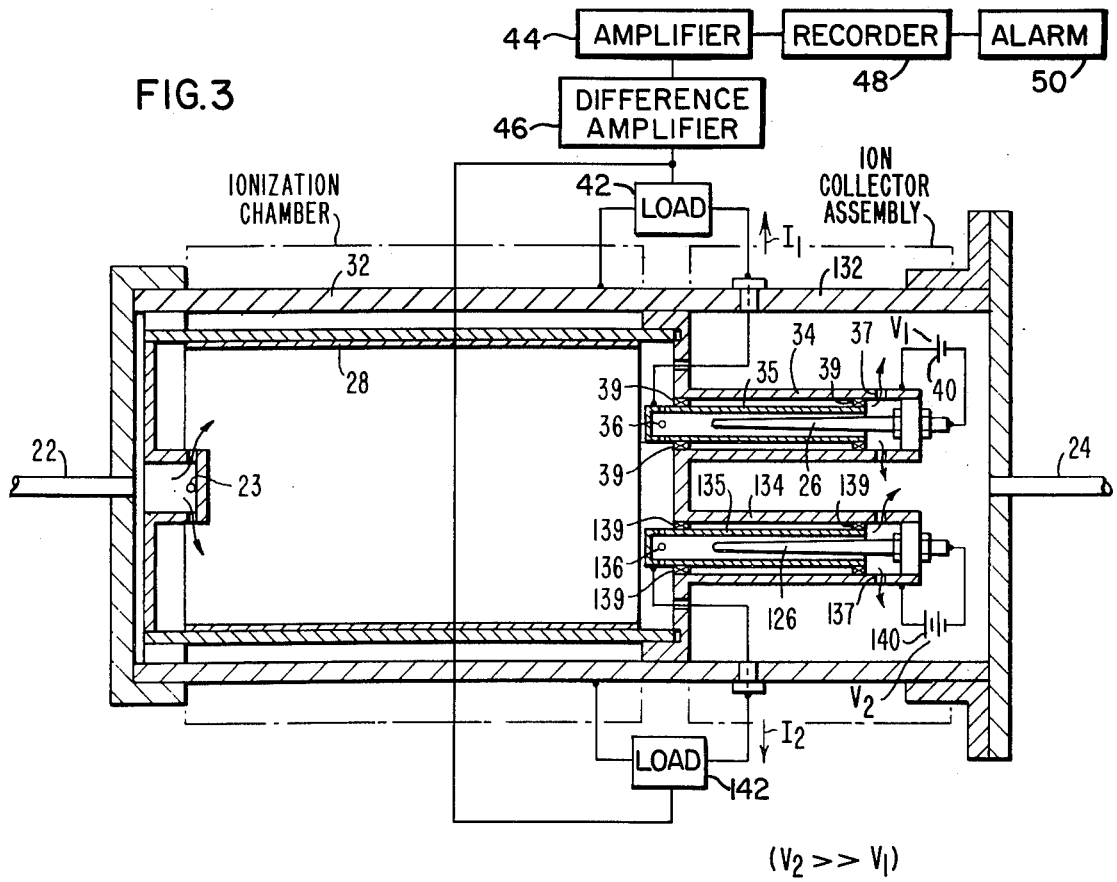
FIG. 3 is a simplified schematic view of the ionization chamber with two parallel ion collectors.

Conduit means to circulate a portion of the gaseous carrier externally of casing 16 is provided by extraction pipe 22 and return pipe 24. The gas that is extracted from the generator is introduced through pipe 22 into an ionization chamber 32 and collector assembly 132 and is subsequently returned to the generator through the outlet pipe 24. Ionization chamber 32 ionizes the cooling gas as it passes through the chamber 32 from conduit 22 into the collector assembly 132. Collector assembly 132 comprises two ion collectors 34 and 134 (FIGS. 2 and 3) which are either connected in series as shown in FIG. 2 or in parallel as shown in FIG. 3.

Voltage $V_1$ is connected to the electrodes of only one collector 34 within assembly 132. Voltage $V_1$ is less than voltage $V_2$ and is selected so that only the cooling gas ions will be deposited in collector 34.

Voltage $V_2$ is connected to the electrodes of a second collector 134 in assembly 132. Voltage $V_2$ is much greater than voltage $V_1$ and is selected so that not only will the cooling gas ions be deposited but also heavier ions. The presence of heavier ions is due to thermoparticulates attaching themselves to ions of the cooling gas.

When the collector assembly 132 comprises the arrangement indicated by FIG. 2, the majority of cooling gas ions will be deposited in collector 34 during the time when there are no thermoparticulates and thus $I_2$ (ionization current in collector 134) will be approximately zero. When there are thermoparticulates, $I_1$ (ionization current in collector 34) will decrease and $I_2$ will increase. Therefore, by amplifying and monitoring $I_2$ with a monitoring means such as a recorder it is possible to detect overheating within a dynamoelectric machine and to initiate an alarm so that corrective action may be taken.

When collector assembly 132 comprises the arrangement indicated by FIG. 3, an approximately equal amount of cooling gas ions will be deposited in collectors 34 and 134 and thus $I_1$ will normally equal $I_2$. When there are thermoparticulates present $I_1$ will decrease and $I_2$ will increase. Therefore, by sensing the difference between $I_1$ and $I_2$, and monitoring this difference with a monitoring means such as a recorder, it is possible to detect overheating within a dynamoelectric machine and to initiate an alarm so that corrective action may be taken.

FIG. 1 shows the general arrangement of detector, decoder and alarm devices responsive to ionization currents $I_1$ and $I_2$.

Referring to FIG. 2, which provides a more detailed view of ionization chamber 32 and collector assembly 132 of FIG. 1, the gas flows into an ionizing chamber 32 through holes 23 and is subjected to a low level radiation by means of a layer 28 of radioactive substance distributed on the inner surface of ionization chamber 32. A suitable low level radiation coating contains Thorium 232 which is an alpha source causing formation of positive and negative ion pairs from gas molecules passing through the ionization chamber 32. Taking the operation of the first collecting chamber 34, we see that gas enters the collecting chamber 34 through holes 36 flowing past the electrode 26 to the gas outlet 37. A positive voltage is imposed between the collector electrode 35 through the collector load 42, and a negative voltage on electrode 26 by means of a DC source 40 of voltage $V_1$. The collector electrode 35 is insulated from the chamber walls with the insulators 39. Negatively charged ions are collected on the collector electrode 35, this action being assisted by the repulsion from the negative charged electrode 26. The current flowing into a collector load 42 may be amplified in an amplifier 44, and recorded on recorder 48.

Similarly, the ionized gas enters collector chamber 134 through holes 136 flowing past the electrode 126 to the gas outlet 137. The gas enters return conduit 24 through gas outlet 137. A positive voltage is imposed on collection chamber 134 and the collector electrode 135 and a negative voltage on electrode 126 by means of a DC source 140. DC source 140 as will be discussed below is of a higher potential than source 40.

The current flowing from the collector electrode 135 into the collector load 142 is amplified in an amplifier 144 and recorded on a recorder 148. The principle of operation of the ionization chambers that was just described is individually the same that is presently used in generator condition monitors. The difference between the prior art and the present invention is in the use of two ion collectors with a different bias applied to each electrode. The benefits of the invention result from the difference in mobility of the cooling gas ions, hydrogen, for example, as compared to that of the charged thermoparticulates. The mobility of hydrogen ions is 13.6 cm$^2$/(volt sec.) in hydrogen at one atmosphere pressure or 2.72 cm$^2$/(volt sec.) at 5 atmospheres. Given the mobility of a charge particle that will be deposited by a given electric field, then the radius of that charge particle is given by the expression:

$$v = \frac{e(1 + 0.85\frac{\lambda}{a})}{6\pi \mu a}$$

Where:
$v$ = mobility in m$^2$ . volt$^{-1}$ . sec$^{-1}$
$\mu$ = viscosity of the hydrogen gas = $0.88 \times 10^{-5}$ Nsec./m$^{-2}$;
$a$ = radius of the particulate = $10^{-7}$ to $10^{-9}$ meters;
$\lambda$ = mean free path which is $\approx 3.4 \times 10^{-8}$ meters;
$e$ = charge of an electron = $1.6 \times 10^{-19}$ Coulombs;
and all in hydrogen at a pressure of 5 atmospheres.

The electrodes used in the collecting chambers may be, for example, coaxial-type cylinders with diameters of 0.63 and 1.23 cm, respectively, and an overall length of 7.3 cm, which corresponds to an interelectrode volume of 6.4 cm$^3$. A typical flow rate through the monitor is 100 cm$^3$/sec., and the residence time for hydrogen in the electrodeposition space will be 0.064 sec. As the electrode spacing is 0.3 cm, an ion velocity of the order of 4.7 cm/sec. is needed to result in a complete deposition of the ions.

With a voltage difference of 10 volts and an electron spacing of 0.3 cm, the potential on the electrodes will be 33.3 volts/cm, causing a velocity of 4.7 cm/sec. to be reached for the ions that have a mobility of 0.141 cm$^2$/(volt sec.), or from the above equation a radius of approximately 1.4 nm. Most particulates have larger radii and consequently lower mobility to be electrodeposited under these circumstances, while hydrogen ions are small enough to be quantitively removed by the electric field that exists between electrodes 26 and 35. On the other hand, an applied voltage of 500 volts to electrode 126 or a field of 1667 volts/cm will deposit ions of charged thermoparticulates with a mobility as low as $2.82 \times 10^{-3}$ cm$^2$/(volt sec.). According to the above equation this corresponds to charged thermoparticulates with a radius of approximately 12.6 nm, well into the typical range of the thermoparticulates which are expected to be produced.

In the invention that is described in FIGS. 1 and 2, two electrodeposition collectors 34 and 134 are used in series in connection with a conventional ionization chamber 32. A relatively low voltage from source 40, but sufficiently high enough to electrodeposit all hydrogen ions (for instance 10 volts), is applied to the electrodes of the first conventional electrodeposition collector. A considerably higher voltage from source 140 is applied to the second collector (for instance 500 volts), but low enough so that no possibility for flashover exists. Flashover at 5 atmospheres of hydrogen would require a voltage greater than 27.2 kv. The second collector can have the same dimensions as the first collector, in which case a voltage of 500 volts will be suitable, but it can also be built with a larger electrode area, in which case a lower voltage can be used for the same effect.

When no thermoparticulates are present, no electrodeposition current will occur at the second collector, as all the gaseous ions will be deposited in the first collector. No change of gas pressure, flow through the monitor, nor effectiveness of the radiation source will change this fact. However, when thermoparticulates are present, the charged thermoparticulates with radii of below 12.6 nm will be deposited out of the gaseous carries in the second collector 134 (with 500 volts provided by power supply 140), causing an electrodeposition current that can be amplified, recorded or used to trigger an alarm. It is evident by variations of the size of the collecting chambers, the bias voltage, and flow rate of the gaseous carries, one ordinarily skilled in the art given the above information can design a system that will detect any size of thermoparticulates that can be encountered in a gas cooled dynamoelectric machine, the only restraint being avoiding flashover.

Using the principles described above, that is, having two chambers, one biased to deposit gaseous ions, the other chamber biased for deposition of charged thermoparticulates, we can alternatively arrange the chambers to be in parallel with the flow of the ionized cooling gas. FIG. 3 shows this parallel arrangement. Given the same typical flow rate through the monitor of 100 cm$^3$/sec., the flow rate through each chamber will be 50 cm$^3$/sec. The resident time for the hydrogen in the electrodeposition space will be 0.128 seconds. As the electrode spacing is 0.3 cm, an ion velocity of the order of 2.35 cm/sec. is needed in order to result in a complete electrodeposition.

With a voltage difference of 10 volts or 33.3 volts/cm to electrode 26, a velocity of 2.35 cm/sec. will be reached for ions that have a mobility of 0.07 cm$^2$/(volt seconds) or, a radius of 2 nm. Most thermoparticulates have larger radii and consequently lower mobility to be electrodeposited under these circumstances, while hydrogen ions are small enough to be quantitively removed by the electric field. On the other hand, an applied voltage of 500 volts to the electrode 126 or an electric field of 1667 volts/cm will deposit ions of charged thermoparticulates with a mobility as low as $1.41 \times 10^{-3}$ cm$^2$/(volt sec.). Accordingly, this corresponds to charged particulates with a radius of about 19 nm, which is also well into the typical range of the particulates.

Referring to FIG. 3, two identical electrodeposition collectors 34 and 134 are used in connection with a conventional ionization chamber 32, such that the ionized gaseous carrier flowing from the ionization chamber divides into the collectors 34 and 134. A relatively low voltage from source 40 but sufficiently high enough to electrodeposit all the gaseous carries ions; for instance 10 volts, if the carrier is hydrogen as is the practice in the large commercial generator industry; is applied to the electrodes of one of the collectors 34. A considerably higher voltage $V_2$ from source 140 is applied to the second collector 134 but low enough so that no possibility for a flashover exists. Because of the high mobility of gaseous ions, all will be deposited in either of the two collectors. As the flow rate of the cooling gas through the two collectors is identical, when no thermoparticulates are present there will be approximately an equal amount of current generated from the gaseous ions that are deposited on the collectors 34 and 134, irrespective of the difference in applied voltages. Any difference between the two currents is generated by difference amplifier 46, amplified by 44, and recorded by 48, but will be 0 when thermoparticulates are absent, and no change of gas pressure, flow through the monitor, nor effectiveness of the radiation source will change.

When thermoparticulates are present, the current in the first collector 34 will decrease considerably. This is because the free ions combine with the thermoparticulates with the resultant particles having a larger radius and a lower mobility. However, the second collector 134, because of the increased voltage on the electrodes, is able to deposit the lightest of the particulates (up to a radius of 19 nm with a voltage of 500 volts), and the electrodeposition current in the second collector will decrease less than the current from the first collector. The difference of the two currents is amplified by amplifier 44 and recorded by recorder 48. The output of the amplifier 44 can be used to trigger an alarm 50 or other suitable indication.

In contrast to the presently used generator condition monitor, this alarm will only be triggered when thermoparticulates are present in the cooling gas. Thus, the teachings of this invention are based upon the differences in the electrodeposition current obtained when one collector is biased to measure only the presence of the gaseous carrier ions and the other collector is biased to measure the presence of all ions including the charged thermoparticulates. In the present example the use of standard available collectors and with adequate bias voltage to insure the adequate performance of the invention was disclosed.

However, it is understood that this invention is not limited to any single type of collectors and electrodes. Any collectors and electrode configurations, sizes, and spacing are equally applicable and may be substituted by one skilled in the art, given the teachings of this invention, the only limitation being that the bias voltage that is applied between the electrodes must not be at a potential that will produce a flashover.

I claim:

1. An apparatus for detecting thermoparticulates in a gaseous carrier, said apparatus comprising:
   a gas ionization chamber which includes a means to effect ionization of the gaseous carrier;
   a first detector means comprising a first electrode, a second electrode, an outer shell, and a voltage applied between said electrodes;
   a second detector means in a series arrangement with said first detector and comprising a third electrode, a fourth electrode, an outer shell, and an applied voltage between said electrodes;
   a conduit means to allow flow of said ionized gas with charged thermoparticulates dispersed therein from said ionization chamber to said first detector;

said first detector's voltage is of such a potential as to ensure substantial electrodeposition of said gaseous carrier's free ions;

a conduit means to allow flow of said charged thermoparticulates dispersed within said gaseous carrier from said first detector to said second detector;

said second detector's voltage is of such a potential as to ensure electrodeposition of said charged thermoparticulates;

a means for detecting current flow between said third and fourth electrodes produced by electrodeposition of said thermoparticulates.

2. Apparatus in accordance with claim 1 wherein: said voltage applied between said electrodes of said second detector means is greater than said voltage applied between said electrodes of said first detector means.

3. An apparatus for detecting thermoparticulates in a gaseous carrier, said apparatus comprising:

a gas ionization chamber which includes a source of radiation to effect ionization of the gaseous carrier;

a first detector means comprising a first electrode, a second electrode, an outer shell, and a voltage applied between said electrodes, said detector is operatively joined to said ionization chamber to receive said ionized gas with thermoparticulates dispersed therein;

a second detector means comprising a third electrode, a fourth electrode, an outer shell, and an applied voltage between said electrodes, said second detector is operatively joined to said first detector to receive said gaseous carrier with charged thermoparticulates dispersed therein;

said first detector's voltage is of such a potential to ensure substantial electrodeposition of said gaseous carrier's free ions; and said second detector's voltage is of such a potential to ensure electrodeposition of said charged thermoparticulates and to produce a current flow through a load connected between said third and fourth electrodes whose magnitude is proportional to the quantity of charged thermoparticulates dispersed within said gaseous carrier.

4. Apparatus in accordance with claim 3 wherein: said voltage applied between said electrodes of said second detector means is greater than said voltage applied between said electrodes of said first detector means.

5. An apparatus for detecting thermoparticulates in a gaseous carrier, said apparatus comprising:

a gas ionization chamber which includes a source of radiation to effect ionization of the gaseous carrier;

a first detector means comprising a first electrode, a second electrode, an outer shell, and a voltage applied between said electrodes, a second detector means comprising a third electrode, a fourth electrode, an outer shell, and an applied voltage between said electrodes, said first and second detectors being operatively joined in parallel arrangement to said ionization chamber;

said first detector's voltage is of such a potential to ensure substantial electrodeposition of said gaseous carrier's free ions; and said second detector's voltage is of such a potential to ensure electrodeposition of said charged thermoparticulates and to produce a current flow through a load connected between said third and fourth electrodes whose magnitude is proportional to the quantity of charged thermoparticulates dispersed within said gaseous carrier.

6. Apparatus in accordance with claim 5 wherein: said voltage applied between said electrodes of said second detector means is greater than said voltage applied between said electrodes of said first detector means, and further comprising means for comparing currents detected by said first and second detector means.

* * * * *